United States Patent
Chun et al.

(10) Patent No.: US 10,106,841 B2
(45) Date of Patent: Oct. 23, 2018

(54) QUANTIFICATION OF TARGET NUCLEIC ACID USING COMMON INTERNAL CONTROL

(71) Applicant: SEEGENE, INC., Seoul (KR)

(72) Inventors: Jong Yoon Chun, Seoul (KR); Young Jo Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 0 days.

(21) Appl. No.: 14/888,488

(22) PCT Filed: May 2, 2014

(86) PCT No.: PCT/KR2014/003968
§ 371 (c)(1),
(2) Date: Nov. 2, 2015

(87) PCT Pub. No.: WO2014/178689
PCT Pub. Date: Nov. 6, 2014

(65) Prior Publication Data
US 2016/0376643 A1    Dec. 29, 2016

(30) Foreign Application Priority Data

May 3, 2013    (KR) .................. 10-2013-0050282

(51) Int. Cl.
*G01N 33/48*    (2006.01)
*C12Q 1/6851*    (2018.01)
*G06G 7/58*    (2006.01)

(52) U.S. Cl.
CPC ................................ *C12Q 1/6851* (2013.01)

(58) Field of Classification Search
CPC .......... G06F 19/18; G06F 19/20; G06F 19/22; G06F 19/24; G01N 33/66; G01N 33/582
See application file for complete search history.

(56) References Cited

U.S. PATENT DOCUMENTS

| 2003/0104438 A1 | 6/2003 | Eyre et al. |
| 2006/0292571 A1 | 12/2006 | Babiel et al. |
| 2011/0136104 A1 | 6/2011 | Pregibon |
| 2012/0101740 A1 | 4/2012 | Orpana et al. |

FOREIGN PATENT DOCUMENTS

WO    2012106428 A2    8/2012

OTHER PUBLICATIONS

Vanguilder, Heather D., et al.; "Twenty-five years of quantitative PCR for gene expression analysis;" Biotechniques, vol. 44, No. 5, pp. 619-626 (2008).
Pfaffl, Michael W., "A new mathematical model for relative quantification in real-time RT-PCR;" Nucleic Acids Research, vol. 29, No. 9, pp. 2002-2007 (2001).
International Search Report, dated Aug. 12, 2014, issued in PCT/KR2014/003968.
Bustin, S.A.; Absolute quantification of mRNA using real-time reverse transcription polymerase chain reaction assays; Journal of Molecular Endocrinology (2000) vol. 25, pp. 169-193.
Pfaffl, M., et al.; Validities of mRNA quantification using recombinant RNA and recombinant DNA external calibration curves in real-time RT-PCR; Biotechnology Letters, 2001, vol. 23, pp. 275-282.
Livak, K., et al.; Analysis of Relative Gene Expression Data Using Real-Time Quantitative PCR and the 2-ΔΔ2Ct Method; Methods, 2001, vol. 25, pp. 402-408.
Souazé, F., et al.; Quantitative RT-PCR: Limits and Accuracy; BioTechniques, 1996, vol. 21, pp. 280-285.

*Primary Examiner* — Eric S Dejong
(74) *Attorney, Agent, or Firm* — Gianna J. Arnold; Saul Ewing Arnstein & Lehr LLP (57) ABSTRACT

The present invention relates to a method for quantifying a target nucleic acid sequence by use of a common internal control. The present invention allows to determine an absolute initial amount of a target nucleic acid sequence with no use of a standard curve. The present invention amplifies not only a control reaction mixture comprising a known-amount standard and an internal control but also a sample reaction mixture comprising an internal control identical to the internal control in the control reaction mixture and the target nucleic acid sequence to be quantified. In the present invention, a relative ratio of the amount of the standard and the amount of the target nucleic acid sequence is calculated by using the internal control and then an initial amount of the target nucleic acid sequence is determined by using a known amount of the standard.

11 Claims, 3 Drawing Sheets
Specification includes a Sequence Listing.

Fig. 1A

Control tube

Standard material (10 pg)

Sample tube

Target (100 pg)

Fig. 1B

Sample tubes

Target(1 pg)

NTC

Fig. 1C

Control tube

| Amount of standard material [1] | $C_T$ value | | $\Delta C_T$ [3] |
|---|---|---|---|
| | IC [2] | Standard material | |
| 10 pg | 28.7 | 30.8 | -2.1 |

[1] Standard material is a genomic DNA of *Neisseria gonorrhoeae*.
[2] IC represents Internal Control.
[3] $\Delta C_T = C_T$ value of IC – $C_T$ value of standard material.

Sample tubes

| Amount of Target [1] | $C_T$ value | | $\Delta C_T$ [3] | $\Delta\Delta C_T$ [4] | Estimated Quantity (pg) [5] | Mean (pg) | SD [6] | CV [7] |
|---|---|---|---|---|---|---|---|---|
| | IC [2] | Target | | | | | | |
| | 28.9 | 27.7 | 1.2 | -3.3 | 98.49 | | | |
| 100 pg | 28.7 | 27.5 | 1.2 | -3.3 | 98.49 | 100.85 | 4.08 | 0.04 |
| | 28.9 | 27.6 | 1.3 | -3.4 | 105.56 | | | |
| | 29.1 | 34.4 | -5.3 | 3.2 | 1.09 | | | |
| 1 pg | 28.8 | 34.3 | -5.5 | 3.4 | 0.95 | 0.99 | 0.08 | 0.08 |
| | 28.9 | 34.4 | -5.5 | 3.4 | 0.95 | | | |
| | 28.5 | - | - | - | - | - | - | - |
| NTC [8] | 28.6 | - | - | - | - | - | - | - |
| | 28.7 | - | - | - | - | - | - | - |

[1] Target is a genomic DNA of *Neisseria gonorrhoeae*.
[2] IC represents Internal Control.
[3] $\Delta C_T = C_T$ value of IC – $C_T$ value of target.
[4] $\Delta\Delta C_T$ = Control tube $\Delta C_T$ – Sample tube $\Delta C_T$.
[5] Estimated initial quantity of Target = 10 pg (the amount of standard material) X $2^{-\Delta\Delta C_T}$
[6] SD represents Standard Deviation
[7] CV represents Coefficient of Variation (CV = SD ÷ Mean).
[8] NTC represents No Target Control.

QUANTIFICATION OF TARGET NUCLEIC ACID USING COMMON INTERNAL CONTROL

CROSS REFERENCE TO RELATED APPLICATIONS

This application claims the priority of PCT/KR2014/003968, filed on May 2, 2014, which claims priority to Korean Patent Application No. 10-2013-0050282, filed May 3, 2013, the entire contents of each of which are hereby incorporated in total by reference.

SEQUENCE LISTING

This application incorporates by reference the Sequence Listing contained in an ASCII text file named "361406_00026_Sequence" submitted via EFS-Web. The text file was created on Sep. 6, 2016, and is 2 kb in size.

BACKGROUND OF THE INVENTION

Field of the Invention

The present invention relates to a method for quantifying a target nucleic acid sequence by use of a common internal control.

Description of the Related Art

A target nucleic acid amplification process is prevalently involved in most of technologies for detecting target nucleic acid sequences. Nucleic acid amplification is a pivotal process for a wide variety of methods in molecular biology, such that various amplification methods have been proposed.

The most predominant process for nucleic acid amplification known as polymerase chain reaction (hereinafter referred to as "PCR") is based on repeated cycles of denaturation of double-stranded DNA, followed by oligonucleotide primer annealing to the DNA template, and primer extension by a DNA polymerase (Mullis et al. U.S. Pat. Nos. 4,683,195, 4,683,202, and 4,800,159; Saiki et al., (1985) Science 230, 1350-1354).

As alternatives, various methods such as LCR (Ligase Chain Reaction), DA (Strand Displacement Amplification), NASBA (Nucleic Acid Sequence-Based Amplification), TMA (Transcription Mediated Amplification) and RCA (Rolling-Circle Amplification) have been suggested.

As application of nucleic acid amplification to target detection, the real-time detection methods are widely utilized to detect a target sequence with measuring nucleic acid amplification in a real-time manner. The real-time detection methods generally use labeled probes specifically hybridized with target sequences. As examples of methods using hybridization between labeled probes and target sequences, the Molecular beacon method using dual-labeled probes capable of hairpin structure (Tyagi et al, *Nature Biotechnology v.* 14 March 1996), the Hybridization probe method using two probes singly labeled with donor or acceptor (Bernad et al, 147-148 *Clin Chem* 2000; 46) and the Lux method using single-labeled oligonucleotides (U.S. Pat. No. 7,537,886) have been developed. In addition, the TaqMan method using cleavage reaction of a dual-labeled probe by the 5'-nuclease activity of DNA polymerases as well as hybridization of dual-labeled probes has been widely employed (U.S. Pat. Nos. 5,210,015 and 5,538,848). Other real-time detection methods is to use labeled primers, for example, including Sunrise primer method (Nazarenko et al, 2516-2521 Nucleic Acids Research, 1997, v. 25 no. 12, and U.S. Pat. No. 6,117,635), Scorpion primer method (Whitcombe et al, 804-807, Nature Biotechnology v. 17 Aug. 1999 and U.S. Pat. No. 6,326,145) and TSG primer method (WO 2011/078441).

As alternative approaches, real-time detection methods using duplexes formed depending on the presence of target nucleic acid sequences have been proposed: Invader assay (U.S. Pat. No. 5,691,142, U.S. Pat. No. 6,358,691 and U.S. Pat. No. 6,194,149), PTOCE (PTO cleavage AND extension) method (WO 2012/096523), PCE-SH (PTO Cleavage and Extension-Dependent Signaling Oligonucleotide Hybridization) method (WO 2013/115442), PCE-NH (PTO Cleavage and Extension-Dependent Non-Hybridization) method (PCT/KR2013/012312).

In the real-time detection methods as homogenous assay, the amplification and detection analysis are performed in a single tube such their performance is relatively convenient. In addition, the real-time detection methods are free from contaminations. As alternatives for target detection in a homogenous assay, the post-PCR melting assay has been suggested in which amplicons are detected using the melting profile (U.S. Pat. No. 5,871,908; U.S. Pat. No. 6,174,670, WO 2012/096523, WO 2013/115442 and PCT/KR2013/012312).

In the meantime, the quantification of target sequences as well as target detection is usually required for prognosis determination and analysis of drug responsiveness in the diagnostic field.

For quantification of target sequences, methods using signals (e.g., $C_t$ value) and standard curve obtained by real-time PCR have been proposed (Bustin, J Mol Endocrinal 25:169 (2000), and Pfaffl and Hageleit, *Biotechn Lett* 23:275 (2001)). Although these quantification approaches are convenient, they have serious problems due to loss in sample extraction step and PCR inhibition.

In addition, there has been suggested a relative quantification method by real-time PCR in which expression level of a certain gene in an unknown sample is compared with that of the certain gene in a control sample. To calculate a relative expression ratio, methods using $\Delta C_P$ (delta $C_P$) or $\Delta\Delta C_t$ (delta delta $C_t$) value with or without efficiency correction have been reported (Livak et al., *Methods,* 25(4):402 (2001), Souaze F et al., *Biotechniques* 21(2): 280 (1996) and Pfaffl M W, AZ of Quantitative PCR pp: 87120 (2004) La Jolla, Calif.: IUL Biotechnology Series, International University Line).

The $\Delta\Delta C_t$ method measures not only expression level of a target gene but also expression level of a reference gene constitutively expressed in cells or tissues, and normalizes expression levels between samples by using the expression level of the reference gene. Generally, housekeeping genes such as the GAPDH gene and β-actin gene are used as the reference gene. They are likely to show different expression levels depending on cells (or tissues) or surrounding environments (reaction conditions and treatments). In this regard, the selection of housekeeping gene or reference gene suitable to analysis purpose and conditions is critical, which is time-consuming and troublesome work. To make matters worse, the selection may not be practical in some situations.

As approaches to detect and quantify target sequences by using PCR, a competitive PCR process using known-amount competitors having a primer binding site identical to that on target sequences has been proposed. While the competitor has a primer binding site identical to that on target sequences, it is differentially detected by difference in internal sequences or size of amplified products. For example, U.S. Pat. No. 5,213,961 discloses a competitive PCR process using gel electrophoresis. A competitive PCR process using post-PCR melting assay has been also proposed to quantify target sequences (Samiya Al-Robaiy et. et., *BioTechniques* 31:1382-1388 (2001)). These methods employ serially-diluted competitors for quantification, which are considered troublesome. As the competitors have a similar sequence to a target sequence for PCR efficiency, heteroduplexes are likely to form. Furthermore, the methods are compelled to use competitors with concentrations similar to those of unknown samples for preventing one of competitors and unknown samples to reach plateau.

Under such circumstances surrounding conventional technologies, there are long-felt needs to absolutely quantify target sequences in more convenient and rapid manner.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventor has made intensive researches to develop methods for quantifying a target nucleic acid sequence in a more convenient and rapid manner. As a result, the present inventor has established a novel protocol using a common internal control in which a control reaction mixture comprises a known-amount standard and an internal control, and a sample reaction mixture comprises an internal control identical to the internal control in the control reaction mixture and the target nucleic acid sequence to be quantified, and the present inventor evaluated the novel quantification process to absolutely determine an initial amount of the target nucleic acid sequence in the nucleic acid sample. The present invention for quantifying the target nucleic acid sequence as alternatives for conventional methods using standard curves can overcome problems associated with conventional methods.

Accordingly, the object of this invention is to provide a method for quantifying a target nucleic acid sequence in a nucleic acid sample using a common internal control.

Other objects and advantages of the present invention will become apparent from the detailed description to follow taken in conjugation with the appended claims and drawings.

DETAILED DESCRIPTION OF THIS INVENTION

In an aspect of this invention, there is provided a method for quantifying a target nucleic acid sequence in a nucleic acid sample using a common internal control, comprising:

(a) preparing (i) a control reaction mixture comprising a known-amount standard and an internal control, and (ii) a sample reaction mixture comprising an internal control identical to the internal control in the control reaction mixture and the target nucleic acid sequence to be quantified in separated vessels respectively, whereby the control reaction mixture and the sample reaction mixture each comprises the common internal control;

(b) performing an amplification reaction by using the control reaction mixture and the sample reaction mixture;

(c) obtaining values reflecting amounts of amplified products of the standard and the internal control in the control reaction mixture, and amplified products of the internal control and the target nucleic acid sequence in the sample reaction mixture, wherein the values are obtained by monitoring the amplification reaction or by analysis after the amplification reaction;

(d) calculating a relative ratio of the amount of the standard and the amount of the target nucleic acid sequence by using values reflecting amounts of amplified products of the standard and the internal control in the control reaction mixture, and values reflecting amounts of amplified products of the internal control and the target nucleic acid sequence in the sample reaction mixture; and (e) determining an initial amount of the target nucleic add sequence in the nucleic acid sample by using a known amount of the standard and the relative ratio calculated in the step (d).

The present inventor has made intensive researches to develop methods for quantifying a target nucleic acid sequence in a more convenient and rapid manner. As a result, the present inventor has established a novel protocol using a common internal control in which a control reaction mixture comprises a known-amount standard and an internal control, and a sample reaction mixture comprises an internal control identical to the internal control in the control reaction mixture and the target nucleic acid sequence to be quantified, and the present inventor evaluated the novel quantification process to absolutely determine an initial amount of the target nucleic acid sequence in the nucleic acid sample. The present invention for quantifying the target nucleic acid sequence as alternatives for conventional methods using standard curves can overcome problems associated with conventional methods.

The present invention will be described in more detail as follows:

Step (a): Preparation of a Control Reaction Mixture and a Sample Reaction Mixture A control reaction mixture comprising a known-amount standard and an internal control, and a sample reaction mixture comprising an internal control identical to the internal control in the control reaction mixture and the target nucleic acid sequence to be quantified are prepared in separated vessels respectively. Therefore, the control reaction mixture and the sample reaction mixture each comprises a common internal control.

The most prominent feature of the present invention is to use not only a common internal control in the control reaction mixture and the sample reaction mixture but also the known-amount standard. According to the present invention, a relative ratio of the amount of the standard and the amount of the target nucleic acid sequence may be calculated by using the common internal control and then the absolute initial amount of the target nucleic acid sequence in the nucleic acid sample may be determined by using the known amount of the standard.

The present invention uses the control reaction mixture and the sample reaction mixture.

The control reaction mixture comprises a known-amount standard and a known-amount or an unknown-amount internal control. The standard exists in the control reaction mixture with a known amount and its known amount is used to determine the absolute initial amount of the target nucleic acid sequence.

The term used herein "amount" includes mass, weight or number. For instance, the amount of a nucleic acid molecule may refer to copy number.

The standard may be a nucleic acid molecule (e.g., DNA or RNA molecule) containing a sequence identical to or different from a target nucleic acid sequence. For example, the standard includes a genome containing a target nucleic acid sequence, a dilution of PCR products of a target nucleic acid sequence or a plasmid carrying a target nucleic acid sequence.

Where the standard comprises a sequence different from a target nucleic acid sequence, it may be any nucleic acid molecule so long as it has a priming sequence identical to a priming sequence of the target nucleic acid sequence. The standard having a priming sequence identical to a priming sequence of the target nucleic acid sequence permits to maintain equal amplification efficiency in the amplification reaction.

According to an embodiment, where another oligonucleotide (e.g., target-specific probe) is used together with primers for detection and quantification of a target nucleic acid sequence, the standard may comprise a sequence identical to a hybridizing sequence (i.e., probing site) of the target nucleic acid sequence with which the another oligonucleotide is hybridized. In such case, the standard and the target nucleic acid sequence may provide values reflecting amounts of amplified products by a single signal generation principle and with equal efficiency.

According to an embodiment, the standard may be a nucleic acid molecule comprising common priming and probing site with a target nucleic acid sequence.

The control reaction mixture comprises a known-amount or an unknown-amount internal control. Such an internal control is contained in both the control reaction mixture and the sample reaction mixture.

The amount of the internal control does not need to be known, because the internal control is used to calibrate or normalize values reflecting amounts of amplified products for calculating a relative ratio of the amount of the standard and the amount of the target nucleic acid sequence. According to an embodiment, even where the amount of the internal control is not known, the internal controls with the same amount may be added to in the control reaction mixture and the sample reaction mixture.

According to an embodiment, the control reaction mixture and the sample reaction mixture contains the same amount of the internal control.

Alternatively, the amount of the internal control may be appropriately preselected in considering an amount of the standard and an expected amount of a target nucleic acid sequence.

According to an embodiment, the control reaction mixture and the sample reaction mixture contains the same amount of the known-amount the internal control.

According to an embodiment, the internal control is an exogenous nucleic acid molecule other than nucleic acid molecule inherently present in sample cells or tissues.

The internal control may be any nucleic acid molecule (e.g., DNA or RNA molecule). The internal control may or may not comprise a priming sequence of the standard and the target nucleic acid sequence.

According to an embodiment, the internal control comprises a priming sequence of the standard and the target nucleic acid sequence. In such case, a single primer pair may be used for simultaneous amplification of the standard and the internal control, and simultaneous amplification of the target nucleic acid sequence and the internal control. In this case, competition between the same primers may occur.

The internal control may be in any length. Specifically, the length of the internal control may be shorter than that of the standard and the target nucleic acid sequence.

According to the present invention, the internal control is not compelled to have a common priming site with the standard (or target nucleic acid sequence). Such a feature permits to quantify at least two target nucleic acid sequences even using a single type of the internal control According to an embodiment, signal indicating the presence of the internal control should be differentiable from signals for the standard and the target nucleic acid sequence. For this, a probing sequence of the internal control is different from probing sequences of the standard and the target nucleic acid sequence.

According to an embodiment, a priming sequence and probing sequence of the standard and the target nucleic acid sequence are the same as each other and different from those of the internal control.

According to an embodiment, where primers (e.g. labeled primers) are used to provide signals for detection, a priming site and probing site are the same as each other.

The sample reaction mixture comprises an internal control identical to the internal control in the control reaction mixture and the target nucleic acid sequence to be quantified.

The expression "an internal control identical to the internal control in the control reaction mixture" includes that the internal control used in the sample reaction mixture is the internal control used in the control reaction mixture, that the internal control in the sample reaction mixture comprises the same sequence as a sequence of the internal control in the control reaction mixture, and that a priming or probe site on the internal control in the sample reaction mixture is the same as that on the internal control in the control reaction mixture.

The present invention uses the common internal control contained in both the control reaction mixture and the sample reaction mixture, calculates a relative ratio of the amount of the standard and the amount of the target nucleic acid sequence by using the common internal control, and then determines an initial amount of the target nucleic acid sequence in the nucleic acid sample by using a known amount of the standard and the relative ratio.

According to an embodiment, the internal control in the control reaction mixture has the same amount as the internal control in the sample reaction mixture.

According to an embodiment, the internal control in the control reaction mixture has different amount from the internal control in the sample reaction mixture. According to an embodiment, in such case, it is necessary to know the difference between the amounts. Where the internal controls with different amounts are used, values reflecting amounts of amplified products of the internal control in the control reaction mixture and the sample reaction mixture should be adjusted by considering difference of the amounts of the internal controls. For example, the amplification reaction is conducted using the internal controls with different amounts, values reflecting amounts of amplified products of the internal controls are obtained, and then one of the values is adjusted to an amended value to be obtained if the same amount of internal controls are used in the control reaction mixture and sample reaction mixture. The adjustment is available because the amounts of the internal controls are to be known.

The term used herein "target nucleic acid", "target nucleic acid sequence" or "target sequence" refers to a nucleic acid sequence of interest for quantification. The target nucleic acid sequence comprises a sequence in a single strand as well as in a double strand. The target nucleic acid sequence comprises a sequence initially present in a nucleic acid sample as well as a sequence newly generated in reactions.

The target nucleic acid sequence to be amplified may include any DNA (gDNA and cDNA), RNA molecules their hybrids (chimera nucleic acid). The sequence may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

Where a mRNA is employed as starting material, a reverse transcription step is necessary prior to performing annealing step, details of which are found in Joseph Sambrook, et al., *Molecular Cloning, A Laboratory Manual*, Cold Spring Harbor Laboratory Press, Cold Spring Harbor, N.Y. (2001); and Noonan, K. F. et al., *Nucleic Acids Res.* 16:10366 (1988)). For reverse transcription, an oligonucleotide dT primer hybridizable to poly A tail of mRNA, random primers or target-specific primers may be used.

The present methods do not require that the template nucleic acid molecules have any particular sequence or length. In particular, the molecules include any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The nucleic acid molecule can also be any nucleic acid molecule which has been or can be recombinantly produced or chemically synthesized. Thus, the nucleic acid sequence may or may not be found in nature.

Step (b): Amplification of the Control Reaction Mixture and the Sample Reaction Mixture The amplification reaction is conducted by using the control reaction mixture and the sample reaction mixture.

According to an embodiment, nucleic acid molecules in the reactions are annealed to or hybridized with primers or probes under a certain amplification or hybridization conditions.

According to an embodiment, the target nucleic acid sequence is amplified by cycles of repeating a series of reactions.

According to an embodiment, the amplification of the target nucleic acid sequence is performed by PCR (polymerase chain reaction), LCR (ligase chain reaction, see Wiedmann M, et al., "Ligase chain reaction (LCR)—overview and applications." PCR Methods and Applications 1994 February; 3(4):S51-64), Barany F. "Genetic disease detection and DNA amplification using cloned thermostable ligase." Proc Natl Acad Sci USA., 88(1):189-93 (1991)), GLCR (gap filling LCR, see WO 90/01069, EP 439182 및 WO 93/00447), Q-beta (Q-beta replicase amplification, see Cahill P, et al., "Polymerase chain reaction and Q beta replicase amplification" *Clin Chem.*, 37(9):1482-5 (1991), U.S. Pat. No. 5,556,751), SDA (strand displacement amplification, see G T Walker et al., "Strand displacement amplification—an isothermal, in vitro DNA amplification technique" Nucleic Acids Res. 20(7):16911696 (1992), EP 497272), 3SR (self-sustained sequence replication, see Mueller J D et al., "Self-sustained sequence replication (3SR): an alternative to PCR" Histochem Cell Biol. 108(4-5):431-7 (1997), NASBA (nucleic acid sequence-based amplification, see Compton, J. "Nucleic acid sequence-based amplification". Nature 350(6313):912 (1991); Keightley, M C et al., "Real-time NASBA detection of SARS-associated coronavirus and comparison with real-time reverse transcription-PCR". Journal of medical virology 77(4):6028 (2005)), TMA (Transcription-Mediated Amplification, see Hofmann W P et al., "Comparison of transcription mediated amplification (TMA) and reverse transcription polymerase chain reaction (RT-PCR) for detection of hepatitis C virus RNA in liver tissue" J Clin Virol. 32(4):289-93 (2005); U.S. Pat. No. 5,888,779).) or RCA (Rolling Circle Amplification, see Hutchison C. A. et al., "Cell-free cloning using phi29 DNA polymerase" Proc. Natl Acad. Sci. USA. 102:1733217336 (2005); Dean F. B., et al., Nelson J. R. et al., "Rapid amplification of plasmid and phage DNA using Phi 29 DNA polymerase and multiply-primed rolling circle amplification. Genome Res. 11:10951099(2001)).

The amplification methods described above may amplify through repeating a series of reactions with or without changing temperatures. The unit of amplification comprising the repetition of a series of reactions is expressed as a "cycle". The unit of cycles may be expressed as the number of the repetition or time being dependent on amplification methods.

The term used herein "cycle" may have a unit as one (1) repetition of a series of reactions or a unit as repetitions of a series of reactions performed in a time interval.

According to an embodiment, the amplification is accomplished under conditions of changed temperatures by the repetition of the series of reactions comprising hybridization between a primer for amplification and the nucleic acid molecule, extension of the primer and dissociation of an extended strand, and the cycle has a unit as one (1) repetition of the series of reactions. One (1) repetition of the series of reactions is expressed as one cycle and two repetitions as two cycles.

According to an embodiment, the amplification is accomplished under isothermal conditions by the repetition of the series of reactions, and the cycle has a unit as repetitions of a series of reactions performed in a time interval. For example, where the unit of the cycle is defined as repetitions of a series of reactions performed in one (1) minute, the repetitions of a series of reactions performed in one (1) minute are expressed as one-minute cycle (or one cycle) and the repetitions of a series of reactions performed in two minutes as two-minute cycles (two cycles).

According to an embodiment, the amplification is performed by PCR. PCR is widely used in the art to amplify nucleic acid molecules and comprises repetition cycles of denaturation of nucleic acid molecules, annealing (hybridization) to nucleic acid molecules and primer extension (U.S. Pat. Nos. 4,683,195, 4,683,202, and 4,800,159; Saiki et al., (1985) Science 230, 1350-1354).

According to an embodiment, the amplification of the nucleic acid molecules in the reactions is performed by a real-time PCR. That is to say, PCR is conducted in the presence of a signal-generating means indicative of the presence of amplified products. The signal-generating means may be used in melting analysis of amplified products.

According to an embodiment, the control reaction mixture comprises a primer (or primer set) for amplification of the standard and a primer (or primer set) for amplification of the internal control, and the sample reaction mixture comprises a primer (or primer set) for amplification of the target nucleic acid sequence and a primer (or primer set) for amplification of the internal control. According to an embodiment, the primer set include a primer pair comprising a forward primer and a reverse primer.

According to an embodiment, the standard has a common priming site with the target nucleic acid sequence such that the standard and the target nucleic acid sequence are amplified by using a common primer set. Where the standard and the target nucleic acid sequence comprise a common priming site, they are amplified by using the common primer set, enabling to decrease variations in amplification reactions and enhance accuracy of quantification.

According to an embodiment, where probes are used to detect the standard and the target nucleic acid sequence (e.g., real-time PCR amplification), the standard and the target nucleic acid sequence may be detected by using an identical probe.

According to an embodiment, the amplification of the control reaction mixture is performed using a primer for the control and a primer for the internal control, and the primer for the standard and the primer for the internal control are the same as or different from each other. Since the present invention employs the control reaction mixture as well as the sample reaction mixture and calibration is done using the common internal control, the standard and the internal control may be amplified using different primers from each other. Where the amplification is performed by multiplex amplification, the primer for the standard and the primer for the internal control may be different from each other. Therefore, a single type of the internal control may be employed for a plural type of the standards. According to an embodiment, the primer for the standard and the primer for the internal control are the same.

According to an embodiment, the amplification of the sample reaction mixture is performed using a primer for the target nucleic acid sequence and a primer for the internal control, and the primer for the target nucleic acid sequence and the primer for the internal control are the same as or different from each other. Specifically, the primer for the target nucleic acid sequence and the primer for the internal control are the same.

A primer is hybridized or annealed to a region on a nucleic acid molecule (template) so that double-stranded structure is formed.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

According to an embodiment, the primer used for the present invention has a dual priming (DPO) structure developed by the present inventor. The oligonucleotide having the DPO structure exhibits much higher target specificity than conventional primers and probes (see WO 2006/095981; Chun et al., Dual priming oligonucleotide system for the multiplex detection of respiratory viruses and SNP genotyping of CYP2C19 gene, *Nucleic Acid Research,* 35:6e40 (2007)).

The term used herein "probe" refers to a single-stranded nucleic acid molecule comprising a portion or portions that are substantially complementary to a target nucleic acid sequence.

According to an embodiment, the primer and probe is an oligodeoxyribonucleotide in a single strand. the primer and probe can be comprised of naturally occurring dNMP (i.e., dAMP, dGM, dCMP and dTMP), modified nucleotide or non-natural nucleotide. For example, the primer and probe may comprise PNA (Peptide Nucleic Acid, see WO 92/20702) or LNA (Locked Nucleic Acid, see WO 98/22489, WO 98/39352 and WO 99/14226). The primer and probe can also include ribonucleotides.

The term "annealing" or "hybridization" as used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

The annealing of the primer for amplification to nucleic acid molecules may be carried out under suitable hybridization conditions routinely determined by optimization procedures. Conditions such as temperature, concentration of components, hybridization and washing times, buffer components, and their pH and ionic strength may be varied depending on various factors, including the length and GC content of oligonucleotide (primers) and the target nucleotide sequence. For instance, when a relatively short oligonucleotide is used, it is preferable that low stringent conditions are adopted. The detailed conditions for hybridization can be found in Joseph Sambrook, et al., *Molecular Cloning, A Laboratory Manual,* Cold Spring Harbor Laboratory Press, Cold Spring Harbor, N.Y. (2001); and M. L. M. Anderson, *Nucleic Acid Hybridization,* Springer-Verlag New York Inc. N.Y. (1999).

There is no intended distinction between the terms "annealing" and "hybridizing", and these terms will be used interchangeably.

The primers used in the present invention have hybridizing nucleotide sequences complementary to the nucleic acid molecule to be amplified. The term "complementary" is used herein to mean that primers or probes are sufficiently complementary to hybridize selectively to a nucleic acid molecule under the designated annealing conditions or stringent conditions, encompassing the terms "substantially complementary" and "perfectly complementary". In an embodiment, the term "complementary" means "perfectly complementary".

The primer annealed to the nucleic acid molecule to be amplified is extended by a template-dependent polymerase, including "Klenow" fragment of *E. coli* DNA polymerase I, a thermostable DNA polymerase, and bacteriophage T7 DNA polymerase. In an embodiment, the template-dependent polymerase is a thermostable DNA polymerase obtained from a variety of bacterial species, including *Thermus aquaticus* (Taq), *Thermus* thermophllus (Tth), *Thermus filiformis, Thermis flavus, Thermococcus literalis, Thermus antranikiank Thermus caldophilus, Thermus chliarophilus, Thermus flavus, Thermus igniterrae, Thermus lacteus, Thermus oshimai; Thermus ruber; Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Thermococcus Thermococcus barossi; Thermococcus gorgonarius, Thermotoga maritima, Thermotoga neapolitana, Therm osiphoafricanus, Pyrococcus woesei; Pyrococcus horikoshk Pyrococcus abyssi; Pyrodictium occultum, Aquifex pyrophllus* and *Aquifex aeolieus*.

When a polymerization reaction is being conducted, the components required for such reaction may be provided in excess in the reaction vessel. Excess in reference to components of the extension reaction refers to an amount of each component such that the ability to achieve the desired extension is not substantially limited by the concentration of that component. It is desirable to provide to the reaction mixture an amount of required cofactors such as $Mg^{2+}$, dATP, dCTP, dGTP, and dTTP in sufficient quantity to support the degree of the extension desired.

Step (c): Obtaining Values Reflecting Amounts of Amplified Products

By monitoring the amplification reaction or by analysis after the amplification reaction, values reflecting amounts of amplified products of the standard and the internal control in the control reaction mixture, and values reflecting amounts of amplified products of the internal control and the target nucleic acid sequence in the sample reaction mixture are obtained.

The values reflecting amounts of amplified products may include any value that is changed depending on amounts of amplified products. For instance, the value reflecting the amount of an amplified product may include a value that is changed depending on the amount of an amplified product in PCR, real-time PCR, electrophoresis or melting analysis.

According to an embodiment, the values for reflecting the amounts of the amplified products are a $C_t$ value in a real-time PCR (polymerase chain reaction) (VanGuilder H D, et al., "Twenty-five years of quantitative PCR for gene expression analysis". *Biotechniques* 44(5):619626 (2008)), an intensity of signal provided by an electrophoresis (e.g., capillary electrophoresis and gel electrophoresis) resultant or an area or peak value of a melting curve (U.S. Pat. Nos. 6,174,670 and 5,789,167, Drobyshev et al., *Gene* 188:45 (1997); Kochinsky and Mirzabekov *Human Mutation* 19:343 (2002); Livehits et al., *J Biomol. Structure Dynam.* 11:783 (1994); and Howell et al., *Nature Biotechnology* 17:87 (1999)).

According to an embodiment, the values for reflecting the amounts of the amplified products include a modified or calculated value. For example, $E^{Ct}$ calculated with considering PCR efficiency instead of $C_t$ may be used as the values for reflecting the amounts of the amplified products (E: PCR efficiency of a nucleic acid in a PCR condition).

The values for reflecting the amounts of the amplified products may be obtained during monitoring of the amplification reaction or in an end-point manner after the amplification reaction. The real-time PCR permits to monitor nucleic acid amplification in a real-time manner by providing signals whose intensity is proportional to amounts of amplified products. Such monitoring provides $C_t$ values (or $C_p$ values). As the electrophoresis or melting analysis may provide signals whose intensity is proportional to amounts of amplified products after amplification, the values for reflecting the amounts of the amplified products may be obtained by analysis after the amplification reaction.

According to an embodiment, the amplified products of the standard and the internal control in the control reaction mixture should be distinguishable from each other for obtaining values reflecting amounts of amplified products of the standard and the internal control in the control reaction mixture. Furthermore, according to an embodiment, the amplified products of the target nucleic acid sequence and the internal control in the sample reaction mixture should be distinguishable from each other for obtaining values reflecting amounts of amplified products of the target nucleic acid sequence and the internal control in the sample reaction mixture. In other words, an indicator is employed to distinguish each of the amplified products. Exemplified indicator may include size of nucleic acid molecules, $T_m$ value and signals provided by labels.

For example, where the values for reflecting the amounts of the amplified products are a $C_t$ value in a real-time PCR, they may be obtained using suitable labels for differentiation of the amplified products. For instance, fluorescent labels with different emission wavelengths may be used for differentiation of the amplified products. Where the values for reflecting the amounts of the amplified products are an intensity of signal provided by electrophoresis resultant, they may be obtained by producing the amplified products with suitable labels and performing electrophoresis to differentiate the amplified products (through difference in electrophoretic mobility depending on nucleic acid size). Where the values for reflecting the amounts of the amplified products are an area or peak value of a melting curve, they may be obtained using $T_m$ difference of the amplified products to differentiate the amplified products.

According to an embodiment, the amplification is carried out in the presence of a signal-generating means to provide signals indicative of the internal control, standard and target nucleic acid sequence, so as to obtain the values for reflecting the amounts of the amplified products. According to an embodiment, the signal-generating means is contacted to the resultant of the step (b) after the amplification.

The term used herein "signal-generating means" refers to any material used in generation of signals indicating the presence of target nucleic acid sequences, for example including oligonucleotides, labels and enzymes. Examples of the oligonucleotides serving as signal-generating means include: oligonucleotides to be specifically hybridized with target nucleic acid sequences (e.g., probes and primers); where oligonucleotides hybridized with target nucleic acid sequences are cleaved to release a fragment, capture oligonucleotides to be specifically hybridized with the fragment; where the fragment hybridized with the capture oligonucleotide is extended to form an extended strand, oligonucleotides to be specifically hybridized with the extended strand; oligonucleotides to be specifically hybridized with the capture oligonucleotide; and combinations thereof.

The label may be linked to oligonucleotides or may be in the free form. The label may be incorporated into extended products during an extension reaction.

Where the cleavage of oligonucleotides is used in signal generation, examples of the enzyme include 5'-nuclease and 3'-nuclease, particularly nucleic acid polymerase having 5'-nuclease activity, nucleic acid polymerase having 3'-nuclease activity or FEN nuclease.

In the present invention, signals may be generated by using various materials described above in various fashions.

According to an embodiment, the signal-generating means is a signal-generating means to generate a signal in a dependent manner on the formation of a duplex.

The signal by the formation of a duplex may be generated by various methods, including Scorpion method (Whitcombe et al, Nature Biotechnology 17:804-807 (1999)), Sunrise (or Amplifluor) method (Nazarenko et al, Nucleic Acids Research, 25(12):2516-2521 (1997), and U.S. Pat. No. 6,117,635), Lux method (U.S. Pat. No. 7,537,886), Plexor method (Sherrill C B, et al., Journal of the American Chemical Society, 126:4550-45569 (2004)), Molecular Beacon method (Tyagi et al, Nature Biotechnology v. 14 Mar. 1996), HyBeacon method (French D J et al., Mol. Cell Probes, 15(6):363-374 (2001)), adjacent hybridization probe method (Bernard, P. S. et al., Anal. Biochem., 273:221 (1999)) LNA method (U.S. Pat. No. 6,977,295), PTOCE (PTO cleavage and extension) method (WO 2012/096523), PCE-SH (PTO Cleavage and Extension-Dependent Signaling Oligonucleotide Hybridization) method (WO 2013/115442) and PCE-NH (PTO Cleavage and Extension-Dependent Non-Hybridization) method (PCT/KR2013/012312).

According to an embodiment, the signal-generating means is a signal-generating means to generate a signal in a dependent manner on cleavage of a detection oligonucleotide.

The signal by the cleavage of the detection oligonucleotide may be generated by various methods, including TaqMan probe method (U.S. Pat. No. 5,210,015), Invader assay (U.S. Pat. No. 5,691,142), PCEC (PTO Cleavage and Extension-Dependent Cleavage) method (WO 2012/134195) and a method described in U.S. Pat. No. 7,309,573.

The label used in the present invention includes various labels known to one of skill in the art. For example, the label includes a chemical label, an enzymatic label, a radioactive label, a magnetic label, a fluorescent label, a luminescent label, and a chemiluminescent label. According to an embodiment, the label includes a single label, an interactive label (e.g., FRET label) and an intercalating dye.

Where the values for reflecting the amounts of the amplified products are an intensity of signal provided by electrophoresis, they may be obtained by producing the amplified products with suitable labels and performing electrophoresis to differentiate the amplified products. In this case, the label useful includes a fluorescent label, a chemical label, a radioactive label, a magnetic label, a luminescent label, a chemiluminescent label and a single label. Intercalating dye can be used after amplification.

According to an embodiment, the values for reflecting the amounts of the amplified products are a $C_t$ value in a real-time PCR, or an area or peak value of a melting curve, and a label useful includes a single label and an interactive label. The single label includes, for example, a fluorescent label, a luminescent label, a chemiluminescent label, an electrochemical label and a metal label. According to an embodiment, the single label provides a different signal (e.g., different signal intensities) depending on its presence on a double strand or single strand. According to an embodiment, the single label is a fluorescent label. The preferable types and binding sites of single fluorescent labels used in this invention are disclosed U.S. Pat. Nos. 7,537,886 and 7,348,141, the teachings of which are incorporated herein by reference in their entity. For example, the single fluorescent label includes JOE, FAM, TAMRA, ROX and fluorescein-based label. The single label may be linked to oligonucleotides by various methods. For instance, the label is linked to probes through a spacer containing carbon atoms (e.g., 3-carbon spacer, 6-carbon spacer or 12-carbon spacer).

As a representative of the interactive label system, the FRET (fluorescence resonance energy transfer) label system includes a fluorescent reporter molecule (donor molecule) and a quencher molecule (acceptor molecule).

The reporter molecule and the quencher molecule useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), Dil (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DiIC (5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. Preferably, the reporter molecule and the quencher molecule include JOE, FAM, TAMRA, ROX and fluorescein-based label.

Suitable fluorescence molecule and suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. R, Handbook of Fluorescent Probes and Research Chemicals, $6^{th}$ Edition (Molecular Probes, Eugene, Oreg., 1996) U.S. Pat. Nos. 3,996,345 and 4,351,760.

It is noteworthy that a non-fluorescent quencher molecule (e.g. black quencher or dark quencher) capable of quenching a fluorescence of a wide range of wavelengths or a specific wavelength may be used in the present invention.

The intercalating dyes intercalate specifically into double-stranded nucleic acid molecules to generate signals. Exemplified intercalating dyes useful in this invention include SYBR™ Green I, PO-PRO™-1, BO-PRO™-1, SYTO™43, SYTO™44, SYTO™45, SYTOX™ Blue, POPO™-1, POPO™-3, BOBO™-1, BOBO™-3, LO-PRO™-1, JO-PRO™-1, YO-PRO™1, TO-PRO™1, SYTO™11, SYTO™ 13, SYTO™ 15, SYTO™ 16, SYTO™ 20, SYTO™23, TOTO™-3, YOYO™3, GelStar™ and thiazole orange.

Steps (d) and (e): Calculation of a Relative Ratio of the Amount of the Standard and the Amount of the Target Nucleic Acid Sequence and Determination of an Initial Amount of the Target Nucleic Acid Sequence The relative ratio of the amount of the standard and the amount of the target nucleic acid sequence is calculated by using values reflecting amounts of amplified products of the standard and the internal control in the control reaction mixture, and values reflecting amounts of amplified products of the internal control and the target nucleic acid sequence in the sample reaction mixture.

The values reflecting amounts of amplified products of the standard and the internal control in the control reaction mixture, and the values reflecting amounts of amplified products of the internal control and the target nucleic acid sequence in the sample reaction mixture may be adjusted in various combinations. With various calculation approaches using the values (or their adjusted values), the relative ratio of the amount of the standard and the amount of the target nucleic acid sequence may be calculated. Then, the initial amount of the target nucleic acid sequence in the nucleic acid sample is determined by using a known amount of the standard and the relative ratio calculated. According to an embodiment, the known amount of the standard and the relative ratio are multiplied or divided to determine the initial amount of the target nucleic acid sequence.

According to an embodiment, the step (d) is performed in such a manner that the value for the standard is calibrated against the value for the internal control in the control reaction mixture and the value for the target nucleic acid sequence is calibrated against the value for the internal control in the sample reaction mixture, followed by calculating the relative ratio of the known amount of the standard and the amount of the target nucleic acid sequence by using the calibrated values.

According to an embodiment, the internal control in the present invention is employed to remove variations between amplification reactions. In considering amplification resultants of the internal controls, the other amplification resultants are calibrated. For example, where the values for reflecting the amounts of the amplified products are a $C_t$ value in a real-time PCR, a $C_t$ value of the standard is calibrated by subtracting a $C_t$ value of the internal control in the control reaction mixture with the $C_t$ value of the standard, and a $C_t$ value of the target nucleic acid sequence is calibrated by subtracting a $C_t$ value of the internal control in the sample reaction mixture with the $C_t$ value of the target nucleic acid sequence. Alternatively, a $C_t$ value of the standard is calibrated by subtracting the $C_t$ value of the standard with a $C_t$ value of the internal control in the control reaction mixture, and a $C_t$ value of the target nucleic acid sequence is calibrated by subtracting the $C_t$ value of the target nucleic acid sequence with a $C_t$ value of the internal control in the sample reaction mixture.

According to an embodiment, when the values for reflecting the amounts of the amplified products are a $C_t$ value in a real-time PCR, the determination of the initial amount of the target nucleic acid sequence in the nucleic acid sample is performed in such a manner that a difference ($\Delta C_t$) between the $C_t$ value for the standard and the $C_t$ value for the internal control in the control reaction mixture (i.e., $\Delta C_{t\ control} : C_{t\ internal\ control} - C_{t\ standard}$ or $C_{t\ standard} - C_{t\ internal\ control}$) is obtained, and a difference ($\Delta C_t$) between the $C_t$ value for the target nucleic acid sequence and the $C_t$ value for the internal control in the sample reaction mixture (i.e., $\Delta C_{t\ sample} : C_{t\ internal\ control} - C_{t\ target\ nucleic\ acid\ sequence}$ or $C_{t\ target\ nucleic\ acid\ sequence} - C_{t\ internal\ control}$) is obtained. The, a difference ($\Delta\Delta C_t$) between the two differences is obtained as follow $\Delta\Delta C_t = \Delta C_{t\ control} - \Delta C_{t\ sample}$ or $\Delta C_{t\ sample} - \Delta C_{t\ control}$. The relative ratio of the amount of the standard and the amount of the target nucleic acid sequence is calculated by using the $\Delta\Delta C_t$ and then the initial amount of the target nucleic acid sequence in the nucleic acid sample is determined by using the known amount of the standard and the $\Delta\Delta C_t$ value (or $-\Delta\Delta C_t$ value).

In the present invention, calculation equations used in conventional methods for relative quantification may be employed to calculate the relative ratio of the amount of the standard and the amount of the target nucleic acid sequence.

According to an embodiment, a so-called "$\Delta\Delta C_t$ method" (Livak K J, et al., (2001) *Methods* 25(4): 402-408) may be used to calculate the relative ratio of the amount of the standard and the amount of the target nucleic acid sequence. In this method, the relative ratio of the amount of the standard and the amount of the target nucleic acid sequence (R) is $2^{-\Delta\Delta Ct}$. For example, where the $C_t$ values of the internal control and the standard in the control reaction mixture are 17 and 23, respectively, $\Delta C_t$ of the control reaction mixture ($\Delta C_{t\ control} = C_{t\ internal\ control} - C_{t\ standard}$) is $-6$. Where the $C_t$ values of the internal control and the target nucleic acid sequence in the sample reaction mixture are 16 and 17, respectively, $\Delta C_t$ of the sample reaction mixture ($\Delta C_{t\ sample} = C_{t\ internal\ control} - C_{t\ target\ nucleic\ acid\ sequence}$) is $-1$. Therefore, $\Delta\Delta C_t$ value ($\Delta\Delta C_t = \Delta C_{t\ control} - \Delta C_{t\ sample}$) is $-5$ and the relative ratio of the amount of the standard and the amount of the target nucleic acid sequence ($R=2^{-\Delta\Delta Ct}$) is 32. Given that the amount of the standard is 100 pg, the initial amount of the target nucleic acid sequence is determined as 3200 pg (32×100 pg).

There were reported conventional approaches for relative quantification using cross point ($C_r$) value with considering PCR efficiency correction (Pfaffl M W., *Nucleic Acids research* 29(9) e45 2001). Where these approaches are adopted to the present invention, the relative ratio of the amount of the standard and the amount of the target nucleic acid sequence (R) may be calculated by the equation $[(E_{target})^{\Delta C_{p\ target}} / (E_{internal\ control})^{\Delta Cp\ internal\ control}]$ [wherein $E_{target}$ is PCR efficiencies of target nucleic acid sequence and standard, $E_{internal\ control}$ is PCR efficiency of internal control, $\Delta C_{p\ target}$ is "$C_p$ of the standard$-C_p$ of the target nucleic acid sequence" and $\Delta C_p$ is "$C_{p\ internal\ control}$ of the internal control in the control reaction mixture$-C_p$ of the internal control in the sample reaction mixture". In the equation, PCR efficiencies of the standard and the target nucleic acid sequence are assumed to be identical, and PCR efficiencies of the internal controls in the control reaction mixture and the sample reaction mixture are also assumed to be identical. According to another embodiment considering PCR efficiency correction, the relative ratio of the amount of the standard and the amount of the target nucleic acid sequence (R) may be calculated by the equation $[(E_{internal\ control\ in\ the\ sample\ reaction\ mixture})^{Cp internal\ control\ in\ the\ sample\ reaction\ mixture} / (E_{target\ nucleic\ acid\ sequence\ in\ the\ sample\ reaction\ mixture})^{Cp target\ nucleic\ acid\ sequence\ in\ the\ sample\ reaction\ mixture} \div (E_{internal\ control\ in\ the\ control\ reaction\ mixture})^{Cpinternal\ control\ in\ the\ control\ reaction\ mixture} / (E_{standard\ in\ the\ control\ reaction\ mixture})^{Cpstandard\ in\ the\ control\ reaction\ mixture}]$ (wherein E is PCR efficiency). Pfaffl M W has suggested equations based on multiple samples (Pfaffl M W AZ of Quantitative PCR pp: 87120 (2004) La Jolla, Calif.: IUL Biotechnology Series, International University Line).

The calculation methods of the efficiency of real-time PCR are disclosed in Michael W. Pfaffl "Real-time PCR" Published by International University Line (Editor: T. Dorak), p 63-82, which is incorporated herein by reference.

According to an embodiment, in the equations described above, $C_t$ values may be replaced by $C_p$ values and vice versa.

As represented in the equations with efficiency correction, for calculating the relative ratio of the amount of the standard and the amount of the target nucleic acid sequence, values for the internal control and the standard obtained in the control reaction mixture, and values for the internal control and the target nucleic acid sequence obtained in the sample reaction mixture may be processed in various manners.

For example, the step (d) may be performed in such a manner that the value for the internal control in the sample reaction mixture is calibrated against the value for the internal control in the control reaction mixture, the value for the target nucleic acid sequence is calibrated against the value for the value for the standard, and then the relative ratio of the amount of the standard and the amount of the target nucleic acid sequence is calculated using the calibrated values (e.g., the first equation described in the case considering efficiency correction). Alternatively, the relative ratio of the amount of the standard and the amount of the target nucleic acid sequence is calculated without calibrating values for the internal control and the standard in the control reaction mixture and values for the internal control and the target nucleic acid sequence in the sample reaction mixture (e.g., the second equation described in the case considering efficiency correction).

Meanwhile, $E^{Ct}$ or $E^{Cp}$ calculated from $C_t$ or $C_p$ value with considering PCR efficiency, can be the value for reflecting the amounts of the amplified products. In such case, processing to calculate the relative ratio using the first or second equation may be expressed as follows: the calculation of the relative ratio of the amount of the standard and the amount of the target nucleic acid sequence may be performed in such a manner that the value for the standard is calibrated against the value for the internal control in the control reaction mixture and the value for the target nucleic acid sequence is calibrated against the value for the internal control in the sample reaction mixture, followed by calculating the relative ratio of the known amount of the standard and the amount of the target nucleic acid sequence by using the calibrated values.

According to an embodiment, when the values for reflecting the amounts of the amplified products are an intensity of signal provided by the electrophoresis resultant, the determination of the initial amount of the target nucleic acid sequence in the nucleic acid sample is performed in such a manner that a ratio of the signal intensity for the standard to the signal intensity for the internal control in the control reaction mixture is obtained, a ratio of the signal intensity for the target nucleic acid sequence to the signal intensity for the internal control in the sample reaction mixture is obtained, and the relative ratio of the amount of the standard and the amount of the target nucleic acid sequence is calculated by using a ratio between the two ratios, followed by determining the initial amount of the target nucleic acid sequence by using the known amount of the standard and the relative ratio.

According to an embodiment, when the values for reflecting the amounts of the amplified products are an area or peak value of the melting curve, the determination of the initial amount of the target nucleic acid sequence in the nucleic acid sample is performed in such a manner that a ratio of the area or peak value of the melting curve for the standard to the area or peak value of the melting curve for the internal control in the control reaction mixture is obtained, a ratio of the area or peak value for the target nucleic acid sequence to the area or peak value for the internal control in the sample reaction mixture is obtained, and the relative ratio of the amount of the standard and the amount of the target nucleic acid sequence is calculated by using a ratio between the two ratios, followed by determining the initial amount of the target nucleic acid sequence by using the known amount of the standard and the relative ratio.

According to an embodiment, a ratio of the area or peak value of the melting curve for the internal control to the area or peak value of the melting curve for the standard in the control reaction mixture is obtained and a ratio of the area or peak value for the internal control to the area or peak value for the target nucleic acid sequence in the sample reaction mixture is obtained.

The area or peak value of the melting curve is proportional to the amount of amplified product that is proportional to the initial amount of the target nucleic acid sequence.

The term "melting analysis" used herein is intended to encompass not only a melting analysis in a narrow sense but also a hybridization analysis, unless otherwise indicated. The melting analysis in a narrow sense refers to a method in which the dissociation of duplexes is measured under increasing stringency conditions by adjusting temperatures. The hybridization analysis in a narrow sense refers to a method in which the association of duplexes is measured under decreasing stringency conditions by adjusting temperatures. The term "melting curve" or "melting peak curve" used herein is intended to encompass not only a melting curve or melting peak curve from a melting analysis in a narrow sense but also a hybridization curve or hybridization peak curve from a hybridization analysis, unless otherwise indicated.

The melting (hybridization) curve analysis and the melting (hybridization) peak analysis will be described with reference to disclosures of U.S. Pat. No. 8,039,215.

According to an embodiment, the present method is performed with no use of a standard curve and allows to determine an absolute initial amount of the target nucleic acid sequence in the nucleic acid sample.

The term "standard curve" refers to a graph or mathematical equation to be obtained by using a plurality of standard materials with different amounts.

The advantages of the present invention may be highlighted in the simultaneous (multiplex) quantification of at least two target nucleic acid sequences. According to an embodiment, the target nucleic acid sequence comprises at least two target nucleic acid sequences. Where the quantification of at least two target nucleic acid sequences is performed in a reaction vessel, each target nucleic acid sequence may be absolutely quantified and the target nucleic acid sequences may be quantified relatively to each other.

The present invention is also useful in quantification of a nucleic acid sequence containing a nucleotide variation. According to an embodiment, the target nucleic acid sequence comprises a nucleotide variation. The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term nucleotide variation used herein includes any variation at a particular location in a nucleic acid sequence. In other words, the term nucleotide variation includes a wild type and its any mutant type at a particular location in a nucleic acid sequence.

The features and advantages of this invention will be summarized as follows:

(a) The present invention allows to determine an absolute initial amount of a target nucleic acid sequence with no use of a standard curve. The present invention amplifies not only a control reaction mixture comprising a known-amount standard and an internal control but also a sample reaction mixture comprising an internal control identical to the internal control in the control reaction mixture and the target nucleic acid sequence to be quantified. In the present invention, a relative ratio of the amount of the standard and the amount of the target nucleic acid sequence is calculated by using the internal control and then an initial amount of the target nucleic acid sequence is determined by using a known amount of the standard.

(b) The internal control used in the present invention is an exogenous nucleic acid molecule other than nucleic acid molecules inherently present in sample cells or tissues and its selection is therefore readily. Furthermore, the amounts of the internal controls contained in the control reaction mixture and the sample reaction mixture can be accurately adjusted. By using the control reaction mixture comprising the standard and the internal control as well as the sample reaction mixture, the present invention can calculate the relative ratio of the amount of the standard and the amount of the target nucleic acid sequence in more convenient and rapid manner.

(c) The present invention uses the common internal control in both the control reaction mixture and the sample reaction mixture and values obtained in the control reaction mixture and the sample reaction mixture are calibrated against the common internal control, such that the internal control may be designed to having a different priming site from the standard (or target nucleic acid sequence). Such a feature enables to quantify a plurality of target nucleic acid sequences even using a single type of an internal control.

(d) The present invention can correct sample variation since the internal control is used in the sample reaction mixture. In addition, instrument variation can be validated and corrected because amplification of the control reaction mixture is performed simultaneously with that of the sample reaction mixture.

(e) The present quantification method may be performed in accordance with post-melting analysis and electrophoresis as well as real-time PCR.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Quantification of a Target Nucleic Acid Sequence Using an Internal Control and a Standard Material Quantification of a target nucleic acid sequence using an Internal Control (IC) and a standard material was examined.

Taq DNA polymerase having a 5' nuclease activity was used for the extension of an upstream primer and downstream primer. Plasmid DNA containing the cellulose synthase 3 (CesA3) gene of *Arabidopsis* was used as a IC. The Genomic DNA of *Neisseria gonorrhoeae* was used as a standard material and a target nucleic acid sequence.

TaqMan probes are labeled with a fluorescent reporter molecule at their 5'-ends and a quencher molecule at their 3'-ends (SEQ ID NO: 3 and 6).

Real-time PCR assay using TaqMan probe was carried out with a control tube containing a known amount of standard material and the IC and with a sample tube containing the target nucleic acid sequence and the IC. $C_T$ values were determined for each nucleic acid sequences in the control and sample tubes. Both tubes contain the same amount of the IC. $\Delta C_T$ value and $\Delta\Delta C_T$ value were calculated as follows:

Control tube $\Delta C_T = C_T$ value of $IC - C_T$ value of the standard material Sample tube $\Delta C_T = C_T$ value of $IC - C_T$ value of the target nucleic acid sequence $\Delta\Delta C_T =$ Control tube $\Delta C_T -$ Sample tube $\Delta C_T$ Initial quantity of the target nucleic acid sequence was calculated using $\Delta\Delta C_T$ and the amount of the standard material as follows:

Initial quantity of a target nucleic acid sequence = the amount of standard material X $2^{-\Delta\Delta C_T}$.

The sequences of upstream primer, downstream primer, and TaqMan probe used in this Example are:

```
CesA3-F
                                        (SEQ ID NO: 1)
5'-ATGGAATCCGAAGGAGAAACCIIIIIAAAGCCGATG-3'

CesA3-R
                                        (SEQ ID NO: 2)
5'-TCCTCTCATACTCGTAGCAAGGCIIIIIAACTGGGAATG-3'

CesA3-P
                                        (SEQ ID NO: 3)
5'-[Quasar670]CATTGTTCCGCAGACTTGCCAGA[BHQ-2]-3'

NG-F
                                        (SEQ ID NO: 4)
5'-TACGCCTGCTACTTTCACGCTIIIIIGTAATCAGATG-3'

NG-R
                                        (SEQ ID NO: 5)
5'-CAATGGATCGGTATCACTCGCIIIIICGAGCAAGAAC-3'

NG-P
                                        (SEQ ID NO: 6)
5'-[FAM]TGCCCCTCATTGGCGTGTTTCG[BHQ-1]-3'
(I: Deoxyinosine)
(CesA3: Cellulose synthase 3 gene of Arabidopsis)
(NG: Neisseria gonorrhoeae)
```

The control tube was prepared in the final volume of 20 μl containing 0.1 pg of plasmid DNA of CesA3 (as an IC), 10 pg of genomic DNA of NG (as a standard material), 10 pmole of upstream primers (SEQ ID NOs: 1 and 4), 10 pmole of downstream primers (SEQ ID NOs: 2 and 5), 5 pmole of TaqMan probes (SEQ ID NOs: 3 and 6), and 10 μl of 2× Master Mix [containing 2.5 mM MgCl$_2$, 200 μM of dNTPs and 1.6 units of Taq DNA polymerase (Solgent, Korea)]. The sample tube was prepared in the final volume of 20 μl containing 0.1 pg of plasmid DNA of CesA3 (as an IC), various amount of genomic DNA of NG (100 pg or 1 pg) (as a target nucleic acid sequence), 10 pmole of upstream primers (SEQ ID NOs: 1 and 4), 10 pmole of downstream primers (SEQ ID NOs: 2 and 5), 5 pmole of TaqMan probes (SEQ ID NOs: 3 and 6), and 10 μl of 2× Master Mix [containing 2.5 mM MgCl$_2$, 200 μM of dNTPs and 1.6 units of Taq DNA polymerase (Solgent, Korea)]. The sample tube was prepared in triplicate.

The tubes were placed in the real-time thermocycler (CFX96, Bio-Rad); the reaction mixtures were denatured for 15 min at 95° C. and subjected to 50 cycles of 30 sec at 95 v, 60 sec at 60° C., 30 sec at 72° C. Detection of the generated signal was performed at 60° C. of each cycle.

Figure 1A:
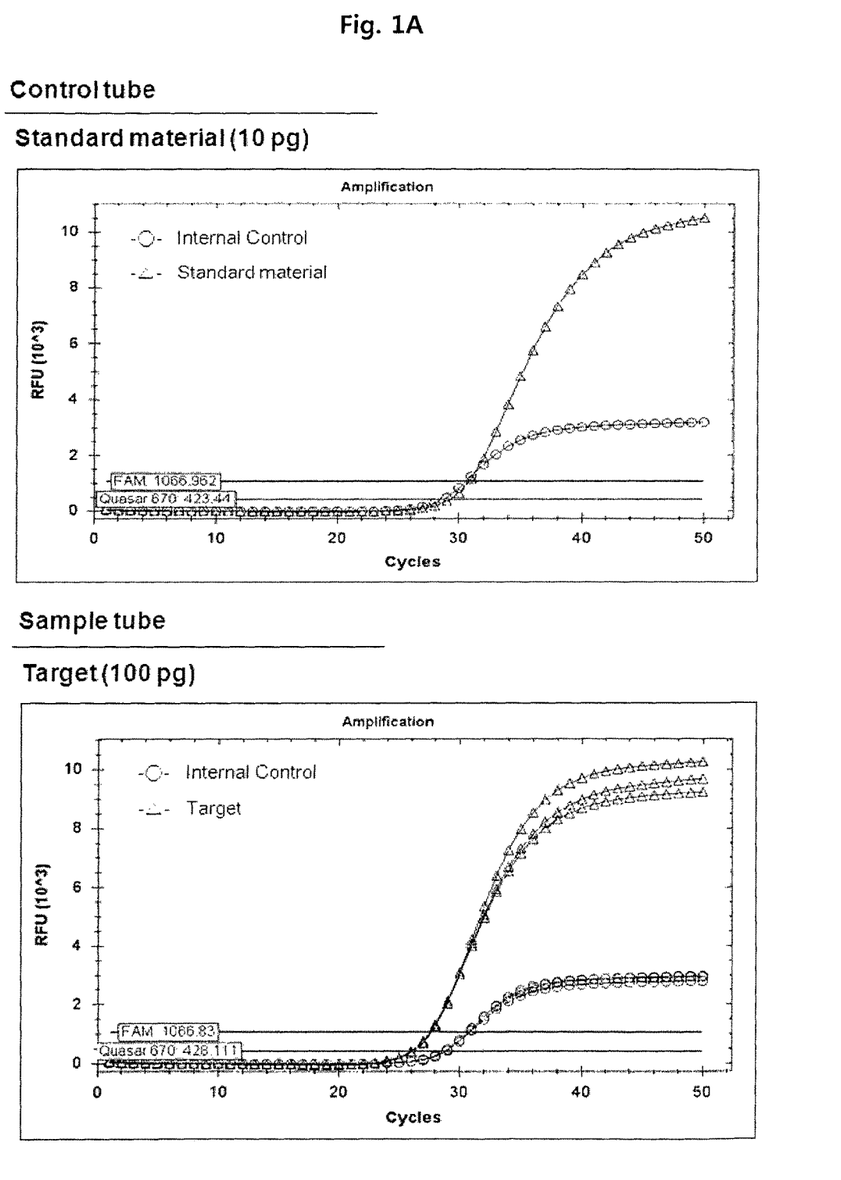
FIG. 1A represents real-time PCR amplification results of the control reaction mixture comprising the internal control and the standard (10 pg) and the sample reaction mixture comprising the internal control and the target nucleic acid sequence (100 pg).
Figure 1B:
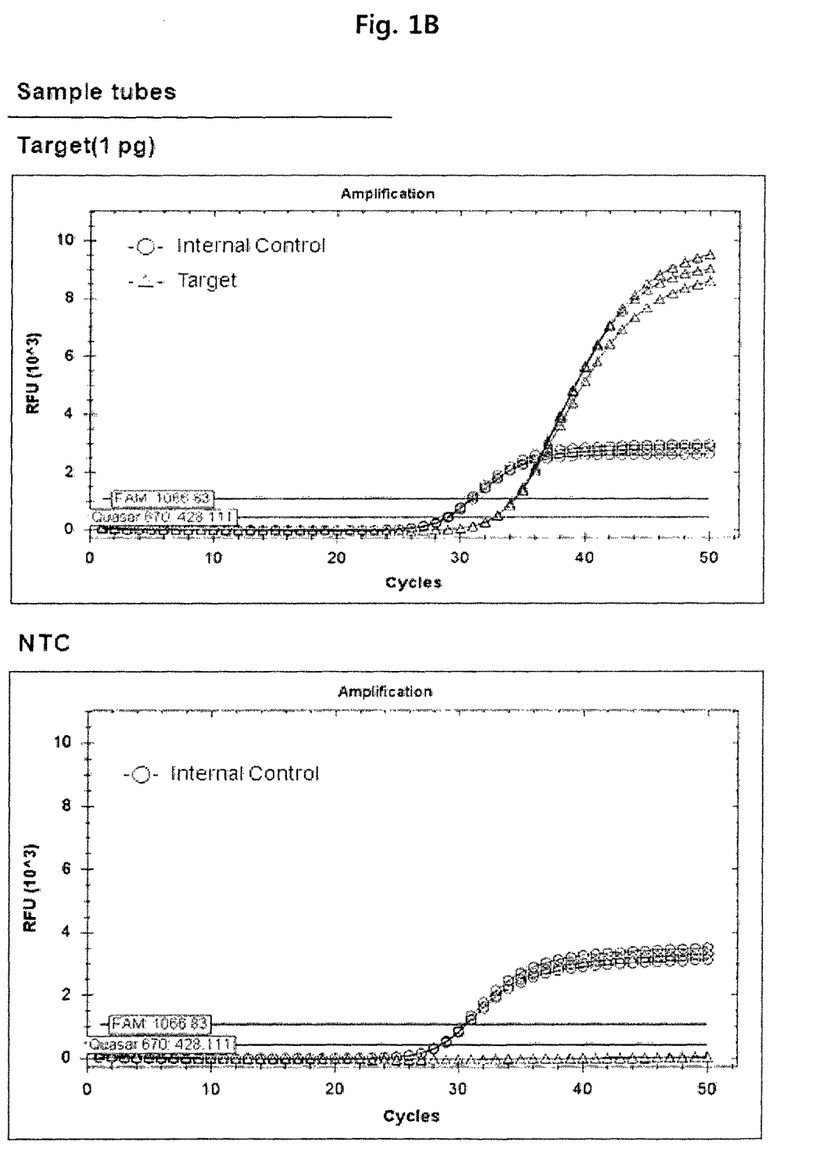
FIG. 1B represents real-time PCR amplification results of the sample reaction mixture comprising the internal control and the target nucleic acid sequence (1 pg) and the reaction comprising the internal control and no target nucleic acid sequence (NTC: No Target Control).
Figure 1C:
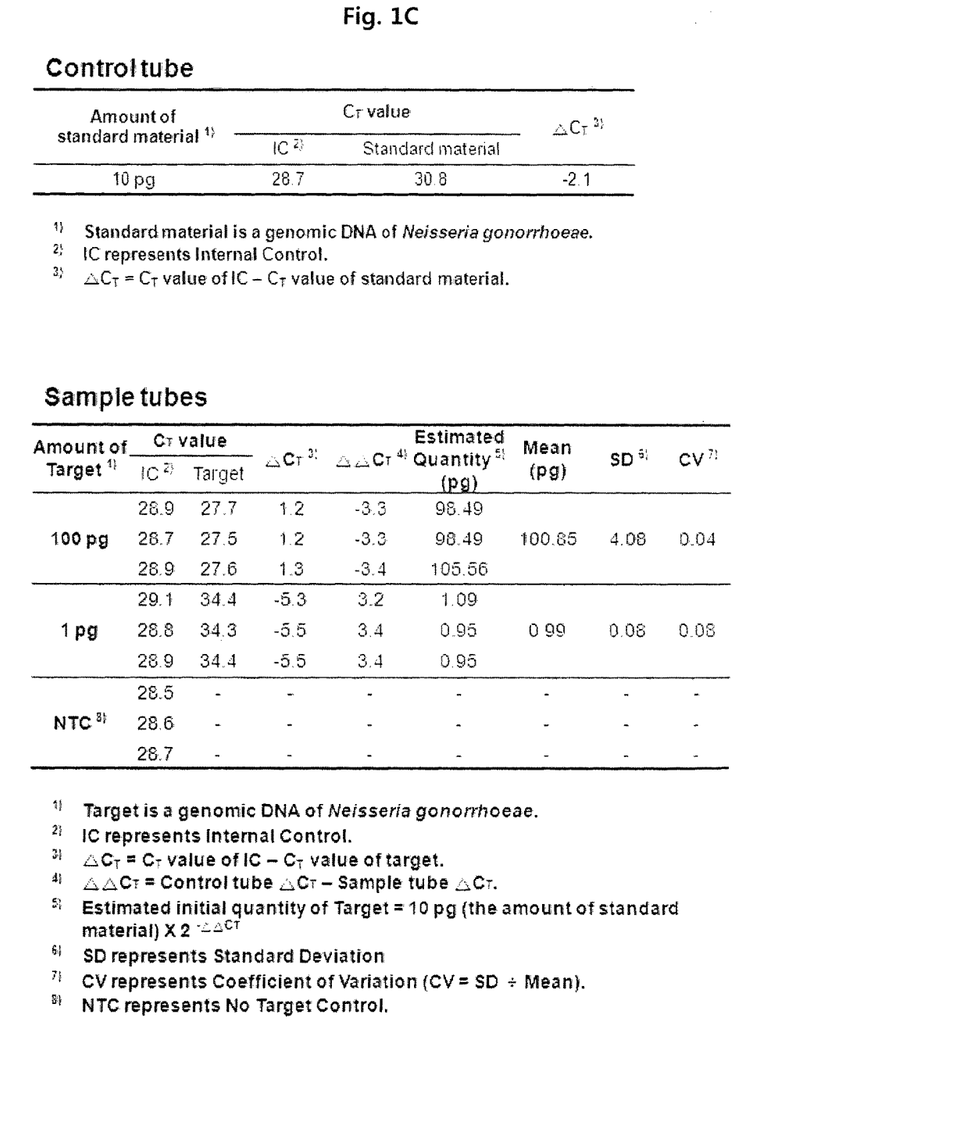
FIG. 1C represents quantification results of the target nucleic acid sequences in the sample reaction mixtures by using values ($C_t$ values) reflecting amounts of amplified products obtained by real-time PCR amplification.

As shown FIG. 1A-1C, $C_T$ values of the IC, the standard material, and the target nucleic acid sequence were obtained and were used to calculate for $\Delta C_T$ values and $\Delta\Delta C_T$ values. Initial quantity of the target nucleic acid sequence was estimated using $\Delta\Delta C_T$ value and the known amount of standard material. The estimated initial quantity of the target nucleic add sequence was approximately same as the amount of the target nucleic acid used in preparing the samples.

This result shows that the quantification method using IC and a known amount of standard material enables measuring the initial quantity of a target nucleic acid sequence.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for quantifying a target nucleic acid sequence in a nucleic acid sample using a common internal control, comprising:
   (a) preparing (i) a control reaction mixture comprising a known-amount standard, an internal control, a primer for amplification of the standard and a primer for amplification of the internal control, and (ii) a sample reaction mixture comprising an internal control identical to the internal control in the control reaction mixture, the target nucleic acid sequence to be quantified, a primer for amplification for the target nucleic acid sequence and a primer for amplification of the internal control in separated vessels respectively, whereby the control reaction mixture and the sample reaction mixture each comprises the common internal control;
   (b) performing an amplification reaction by using the control reaction mixture and the sample reaction mixture wherein the control reaction mixture is subject to the amplification reaction by using the primer for the standard and the primer for the internal control: wherein the sample reaction mixture is subjected to the amplification reaction by using the primer for the target nucleic acid sequence and the primer for the internal control: wherein the primer for the standard and the primer for the internal control are different from each other; and wherein the primer for the target nucleic acid sequence and the primer for the internal control are different from each other;
   (c) obtaining values reflecting amounts of amplified products of the standard and the internal control in the control reaction mixture, and values reflecting amounts of amplified products of the internal control and the target nucleic acid sequence in the sample reaction mixture, wherein the values are obtained by monitoring the amplification reaction or by analysis after the amplification reaction;
   (d) calculating a relative ratio of the amount of the standard and the amount of the target nucleic acid sequence by using the values reflecting amounts of amplified products of the standard and the internal control in the control reaction mixture, and the values reflecting amounts of amplified products of the internal control and the target nucleic acid sequence in the sample reaction mixture; and
   (e) determining an initial amount of the target nucleic acid sequence in the nucleic acid sample by using a known amount of the standard and the relative ratio calculated in the step (d);
   wherein said method occurs without the use of a standard curve.

2. The method according to claim 1, wherein the values for reflecting the amounts of the amplified products are a $C_t$ value in a real-time PCR (polymerase chain reaction), an intensity of signal provided by an electrophoresis resultant or an area or peak value of a melting curve.

3. The method according to claim 1, wherein the step (d) is performed in such a manner that the value for the standard is calibrated against the value for the internal control in the control reaction mixture and the value for the target nucleic acid sequence is calibrated against the value for the internal control in the sample reaction mixture, followed by calculating the relative ratio of the amount of the standard and the amount of the target nucleic acid sequence by using the calibrated values.

4. The method according to claim 1, wherein the values for reflecting the amounts of the amplified products are a $C_t$ value in a real-time PCR, and wherein the determination of the initial amount of the target nucleic acid sequence in the nucleic acid sample is performed in such a manner that a difference ($\Delta C_t$) between the $C_t$ value for the standard and the $C_t$ value for the internal control in the control reaction mixture is obtained, a difference ($\Delta C_t$) between the $C_t$ value for the target nucleic acid sequence and the $C_t$ value for the internal control in the sample reaction mixture is obtained, and the relative ratio of the amount of the standard and the amount of the target nucleic acid sequence is calculated by using a difference ($\Delta\Delta C_t$) between the two differences, followed by determining the initial amount of the target nucleic acid sequence by using the known amount of the standard and the $\Delta\Delta C_t$ value.

5. The method according to claim 1, wherein the values for reflecting the amounts of the amplified products are an intensity of signal provided by the electrophoresis resultant, and wherein the determination of the initial amount of the target nucleic acid sequence in the nucleic acid sample is performed in such a manner that a ratio of the signal intensity for the standard to the signal intensity for the internal control in the control reaction mixture is obtained, a ratio of the signal intensity for the target nucleic acid sequence to the signal intensity for the internal control in the sample reaction mixture is obtained, and the relative ratio of the amount of the standard and the amount of the target nucleic acid sequence is calculated by using a ratio between the two ratios, followed by determining the initial amount of the target nucleic acid sequence by using the known amount of the standard and the relative ratio.

6. The method according to claim 1, wherein the values for reflecting the amounts of the amplified products are an area or peak value of the melting curve, and wherein the determination of the initial amount of the target nucleic acid sequence in the nucleic acid sample is performed in such a manner that a ratio of the area or peak value of the melting curve for the standard to the area or peak value of the melting curve for the internal control in the control reaction mixture is obtained, a ratio of the area or peak value for the target nucleic acid sequence to the area or peak value for the internal control in the sample reaction mixture is obtained, and the relative ratio of the amount of the standard and the amount of the target nucleic acid sequence is calculated by using a ratio between the two ratios, followed by determining the initial amount of the target nucleic acid sequence by using the known amount of the standard and the relative ratio.

7. The method according to claim 1, wherein the standard has a common priming site with the target nucleic acid sequence and wherein the standard and the target nucleic acid sequence are amplified by using a common primer.

8. The method according to claim 1, wherein the internal control in the control reaction mixture has the amount same as the internal control in the sample reaction mixture.

9. The method according to claim 1, wherein the amplification is performed by PCR (polymerase chain reaction), LCR (ligase chain reaction), GLCR (gap filling LCR), Q-beta (Q-beta replicase amplification), SDA (stand displacement amplification), 3SR (self-sustained sequence replication), NASBA (nucleic acid sequence-based amplification), TMA (Transcription-Mediated Amplification) or RCA (Rolling Circle Amplification).

10. The method according to claim 9, wherein the amplification is performed by PCR.

11. The method according to claim 10, wherein the amplification is performed by a real-time PCR.

* * * * *

SEQUENCE LISTING

```
<160> NUMBER OF SEQ ID NOS: 6

<210> SEQ ID NO 1
<211> LENGTH: 36
<212> TYPE: DNA
<213> ORGANISM: Artificial Sequence
<220> FEATURE:
<223> OTHER INFORMATION: CesA3-F; Artificially Synthesized
<220> FEATURE:
<221> NAME/KEY: misc_feature
<222> LOCATION: (22)..(26)
<223> OTHER INFORMATION: n denotes deoxyinosine

<400> SEQUENCE: 1
atggaatccg aaggagaaac cnnnnnaaag ccgatg                              36

<210> SEQ ID NO 2
<211> LENGTH: 39
<212> TYPE: DNA
<213> ORGANISM: Artificial Sequence
<220> FEATURE:
<223> OTHER INFORMATION: CesA3-R; Artificially Synthesized
<220> FEATURE:
<221> NAME/KEY: misc_feature
<222> LOCATION: (24)..(28)
<223> OTHER INFORMATION: n denotes deoxyinosine

<400> SEQUENCE: 2
tcctctcata ctcgtagcaa ggcnnnnnaa ctgggaatg                           39

<210> SEQ ID NO 3
<211> LENGTH: 23
<212> TYPE: DNA
<213> ORGANISM: Artificial Sequence
<220> FEATURE:
<223> OTHER INFORMATION: CesA3-P; Artificially Synthezied

<400> SEQUENCE: 3
cattgttccg cagacttgcc aga                                            23

<210> SEQ ID NO 4
<211> LENGTH: 37
<212> TYPE: DNA
<213> ORGANISM: Artificial Sequence
<220> FEATURE:
<223> OTHER INFORMATION: NG-F; Artificially Synthesized
<220> FEATURE:
<221> NAME/KEY: misc_feature
```

```
<222> LOCATION: (22)..(26)
<223> OTHER INFORMATION: n denotes deoxyinosine

<400> SEQUENCE: 4
tacgcctgct actttcacgc tnnnnngtaa tcagatg                              37

<210> SEQ ID NO 5
<211> LENGTH: 37
<212> TYPE: DNA
<213> ORGANISM: Artificial Sequence
<220> FEATURE:
<223> OTHER INFORMATION: NG-R; Artificially Synthesized
<220> FEATURE:
<221> NAME/KEY: misc_feature
<222> LOCATION: (22)..(26)
<223> OTHER INFORMATION: n denotes deoxyinosine

<400> SEQUENCE: 5
caatggatcg gtatcactcg cnnnnncgag caagaac                              37

<210> SEQ ID NO 6
<211> LENGTH: 22
<212> TYPE: DNA
<213> ORGANISM: Artificial Sequence
<220> FEATURE:
<223> OTHER INFORMATION: NG-P; Artificially Synthesized

<400> SEQUENCE: 6
tgcccctcat tggcgtgttt cg                                              22
```